(12) United States Patent
Rebinsky et al.

(10) Patent No.: US 8,638,111 B2
(45) Date of Patent: Jan. 28, 2014

(54) ZINC OXIDE SULFUR SENSOR MEASUREMENT SYSTEM

(75) Inventors: Douglas Alexander Rebinsky, Peoria, IL (US); Yong Tian, Peoria, IL (US); Orhan Altin, Denizli (TR); Xiaodong Liu, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 13/354,821

(22) Filed: Jan. 20, 2012

(65) Prior Publication Data

US 2012/0174656 A1 Jul. 12, 2012

Related U.S. Application Data

(63) Continuation-in-part of application No. 12/817,936, filed on Jun. 17, 2010.

(51) Int. Cl.
*G01R 27/08* (2006.01)

(52) U.S. Cl.
USPC .......... 324/693; 204/422; 204/426; 205/786.5

(58) Field of Classification Search
USPC ............. 324/693; 204/422, 426; 205/786.5; 73/61.41
See application file for complete search history.

(56) References Cited

U.S. PATENT DOCUMENTS

| | | | | |
|---|---|---|---|---|
| 4,358,951 A | * | 11/1982 | Chang | 73/31.05 |
| 4,947,104 A | * | 8/1990 | Pyke | 324/71.5 |
| 5,140,393 A | * | 8/1992 | Hijikihigawa et al. | 257/252 |
| 6,716,336 B2 | * | 4/2004 | Hurland et al. | 205/786.5 |
| 6,914,279 B2 | * | 7/2005 | Lu et al. | 506/39 |
| 7,172,813 B2 | | 2/2007 | Burgener, II et al. | |
| 7,246,524 B1 | * | 7/2007 | Kholwadwala et al. | 73/715 |
| 7,261,857 B2 | | 8/2007 | Suslick et al. | |
| 7,309,621 B2 | * | 12/2007 | Conley et al. | 438/99 |
| 7,498,824 B2 | * | 3/2009 | Lane | 324/715 |
| 2003/0217922 A1 | * | 11/2003 | Suganuma et al. | 204/426 |
| 2004/0108505 A1 | * | 6/2004 | Tuller et al. | 257/76 |
| 2007/0278490 A1 | * | 12/2007 | Hirao et al. | 257/64 |

(Continued)

FOREIGN PATENT DOCUMENTS

| | | |
|---|---|---|
| JP | 4066857 A | 3/1992 |
| JP | 2004245726 A | 9/2004 |

(Continued)

OTHER PUBLICATIONS

Preetam Singh, et al., "In Situ high temperature XRD studies of ZNO nanopowder prepared via cost effective ultrasonic mist chemical vapour deposition", Bul. Mater. Sci., vol. 31, No. 3, Jun. 2008, pp. 537-577.

J.Y. Kim, et al., "Orientations of Polycrystalline ZNO at the Buried Interface of Oxide Thin Film Transistors (TFTs): A Grazing Incidence X-ray Diffraction Study", Bull. Korean Chem. Soc. 2008, vol. 29, No. 4, pp. 727-728.

(Continued)

*Primary Examiner* — Richard Isla Rodas
(74) *Attorney, Agent, or Firm* — Miller, Matthias & Hull (57) ABSTRACT

A measurement system is disclosed for determining a sulfur concentration in a liquid, such as a liquid fuel. The measurement system includes a first electrode that is at least partially coated with zinc oxide and, more specifically, zinc oxide microstructures. The zinc oxide microstructures have a crystal lattice structure that is oriented in the (002) plane. The first electrode may be connected to an electrometer which, in turn, may be connected to a second electrode. The second electrode may be disposed on a common substrate with the first electrode or may be in the form of a plate disposed substantially parallel to the first electrode.

24 Claims, 9 Drawing Sheets

(56) References Cited

U.S. PATENT DOCUMENTS

| | | |
|---|---|---|
| 2008/0006531 A1 | 1/2008 | Holt |
| 2009/0286351 A1 | 11/2009 | Hirao et al. |
| 2011/0012625 A1 | 1/2011 | Hastings et al. |

FOREIGN PATENT DOCUMENTS

| | | |
|---|---|---|
| JP | 2004294364 A | 10/2004 |
| JP | 2006275950 A | 10/2006 |
| KR | 10-0779090 B1 | 11/2007 |

OTHER PUBLICATIONS

Yuneng Chang, et al., "Key Factors to Grow (002) Zinc Oxide Films by MOCVD at 320° C. and Atmospheric Pressure", Lunghwa University of Science Technology, Dep. Of Chemical Engineering, No. 300, Sec. 1, Wanshow Rd., Gueishan, Taoyuan, 333, Taiwan, R.O.C.

James R. Connoly, Elementary Crystallography for X-Ray Diffraction, for EPS400-001, Introduction to X-Ray Powder Diffraction, Spring 2007.

SCINTAG, Inc., "Chapter 7: Basis of X-ray Diffraction", 1999, pp. 7.1-7.25, Cupertino, California USA.

* cited by examiner

ZINC OXIDE SULFUR SENSOR MEASUREMENT SYSTEM

CROSS-REFERENCE TO RELATED APPLICATIONS

This is a continuation-in-part of application Ser. No. 12/817,936, filed on Jun. 17, 2010, still pending.

TECHNICAL FIELD

This disclosure relates generally to sensors and measurement systems for detecting and measuring sulfur concentrations in liquids. More specifically, this disclosure relates to sulfur measurement systems with improved zinc oxide sulfur sensors for measuring sulfur concentrations in liquids and methods of manufacturing improved sulfur measurement systems that may be used by operators in the field.

BACKGROUND

It is important to be able to accurately and reliably measure the concentration of sulfur in liquids, as various chemical reactions may take place that can release harmful sulfur compounds into the atmosphere or onto physical structures around the sulfur-containing liquid. For example, the combustion of diesel fuel typically generates sulfur oxides ($SO_2$, $SO_3$) and sulfuric acid ($H_2SO_4$), which are components of acid rain and subject to environmental regulations. Further, these sulfur compounds have been linked to catalyst poisoning in diesel particulate filters (DPFs) and sulfuric acid may corrode engine components, such as the cooler and piston ring liner components. These phenomena may occur when using both high sulfur (>350 ppm) and low sulfur (15-350 ppm) fuels.

For these reasons, including the sensitivity of after-treatment components to sulfur compounds, modern diesel engines are now being designed to use ultra low sulfur diesel (ULSD) fuel (<15 ppm S). As a result of these design changes, a low sulfur concentration in diesel fuel is now imperative for optimum performance of many modern diesel engines. While sulfur detection in liquids at levels below 15 ppm is attainable in a laboratory or other test setting, such detection is not currently available in the field with an accurate, portable, reliable, fast and/or inexpensive sensor. Examples of known means of detecting sulfur at ultra-low levels include flame photometry detection (FPD) and inductively coupled plasma (ICP) devices, both of which are appropriate for use in a laboratory setting because of the size of the equipment and the duration of the test cycles.

Accordingly, there is a need for sulfur measurement systems that are compact, easy to use and that are capable of fast measurements of sulfur compound concentrations in diesel fuels by equipment operators in the field.

SUMMARY OF THE DISCLOSURE

In one aspect, a sulfur concentration measurement system for liquids is disclosed. The sulfur concentration measurement system may include a substrate that is at least partially coated with zinc oxide. If the substrate is an insulator, first and second electrodes may be disposed in spaced apart positions between the substrate and the zinc oxide coating. Either a current source or a voltage source is applied between the first and second electrodes and an electrometer, voltmeter or potentiometer may be included for measuring a voltage or current between the first and second electrodes, which may be correlated to the sulfur concentration in the liquid.

In another aspect of this disclosure, a sulfur concentration measurement system is disclosed that includes a sensor that may include a plate-shaped first electrode at least partially coated with zinc oxide. The zinc oxide may have microstructures that have crystal lattice structures oriented in the (002) plane and the sensor may also include a plate-shaped second electrode that is spaced apart and disposed substantially parallel to the first electrode. An open circuit potential between the first and second electrodes is generated by the adsorbed zinc oxide. After a short time period, the voltage stabilizes. The stabilized voltage levels and/or the time it takes for the voltage to stabilize can be used to measure the concentration of sulfur compounds in the liquid.

In yet another aspect, a method for determining a sulfur concentration in a liquid is disclosed. The method includes exposing the liquid to a sulfur sensor. The sensor may include a first electrode at least partially covered with zinc oxide microstructures that protrude from the first electrode. At least some of the zinc oxide microstructures may have a crystal lattice structure oriented in the (002) plane. The sulfur sensor may also have a second electrode in a variety of forms. First, if one electrode (a "working" electrode) is formed on an insulating substrate, a second ("reference") electrode may also be formed on the substrate in a spaced apart position from the first electrode. Then, both electrodes and the substrate are at least partially covered with the zinc oxide coating. Second, the first electrode may be conductive and at least partially covered with the zinc oxide coating or the first electrode may be deposited on an insulating substrate before being covered with the zinc oxide. A second electrode may be coupled to but spaced apart from the first electrode/substrate and disposed at least substantially parallel to the first electrode/substrate. If the first and second electrodes are both deposited on an insulating substrate beneath the zinc oxide coating, the method may further include applying a constant current between the first and second electrodes, monitoring a voltage between the first and second electrodes and, after the voltage has stabilized, correlating the stabilized voltage to a sulfur concentration in the liquid. If the substrate/first electrode/zinc oxide coating is physically spaced apart from the second electrode, no current source or voltage source is needed and the stabilized voltage between the first and second electrodes may be measured with a voltmeter, electrometer or potentiometer.

DETAILED DESCRIPTION

Figure 1:
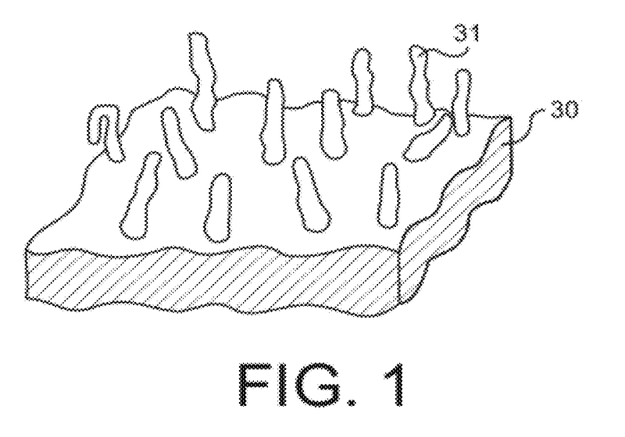
FIG. 1 is a cross-sectional illustration of zinc oxide microstructures on a substrate or first electrode as disclosed herein.

FIG. 1 shows a cross section of a substrate 30, that may be a first electrode that is at least partially coated with a plurality of zinc oxide microstructures 31. The microstructures 31 protrude upwardly from the substrate 30 or electrode. While the term "microstructures" is used herein to describe the nature in size of the zinc oxide protrusions, one skilled in the art will understand that the actual scale of the zinc oxide protrusions 31 may approach or enter the nano-scale or alternatively, be larger than the micro-scale.

Figure 2:
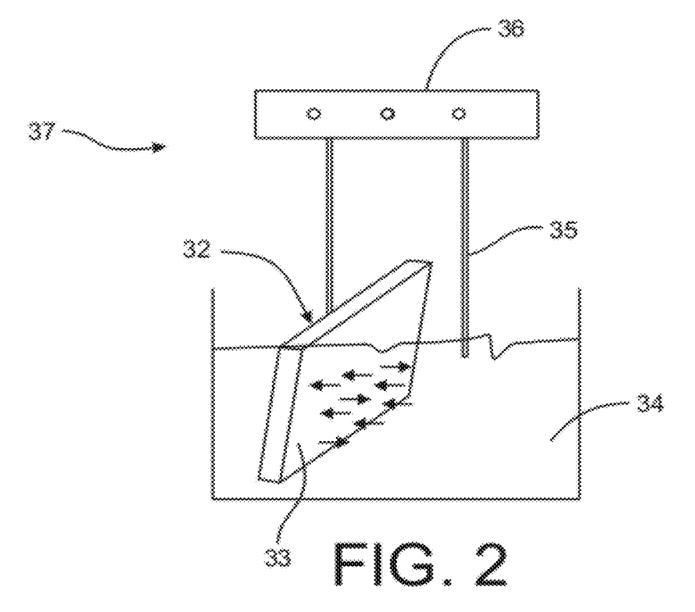
FIG. 2 is a schematic illustration of one method of open circuit potential measurement whereby a disclosed sensor is at least partially submerged in a liquid to be measured and is connected to a first electrode, which is connected to a potentiometer which, in turn, is connected to a second electrode that is at least partially submerged in the liquid.

The substrate 30 may be conductive or non-conductive. Non-conductive substrates 30 may be ceramic or any of a variety of non-conductive substrates that are apparent to those skilled in the art. Conductive substrates may also vary greatly and may eliminate the need for extra process steps to form a first electrode 32 (see FIG. 2) or a separate manufacturing step wherein a first electrode 32 is attached or coupled to the substrate 30 or deposited onto the substrate beneath the zinc oxide protrusions 31. FIG. 2 is an open circuit potential system and requires no voltage or current input. The "first" electrode 32 is commonly referred to as a working electrode; the "second" electrode is commonly referred to as a reference electrode. When the zinc oxide microstructures 31 adsorb sulfur compounds, a potential is generated and can be measured using the system shown in FIG. 2.

Figure 23:
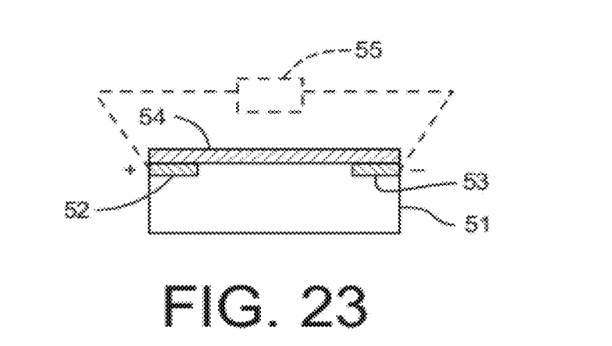
FIG. 23 is a side view of a disclosed sensor constructed of an insulating substrate, two spaced-apart electrodes formed on the substrate and a disclosed zinc oxide coating that at least partially covers the electrodes and substrate.
Figure 24:
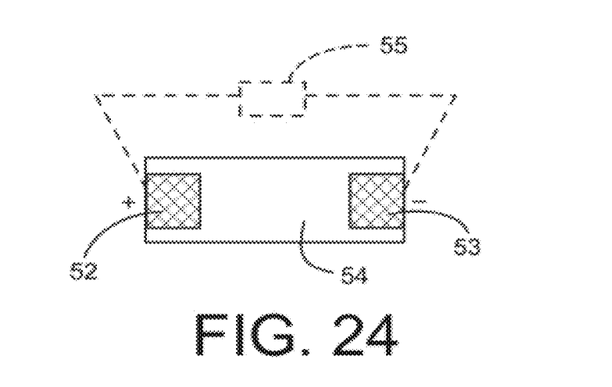
FIG. 24 is a top view of the sensor of FIG. 23, wherein the electrodes are disposed beneath the zinc oxide coating and are shown in phantom.

Another disclosed measurement system is shown in FIGS. 23-24. In this system, an insulating substrate 51 is employed. Two electrodes 52, 53 are deposited onto the substrate 51 before a zinc oxide layer 54 is deposited thereon. Either a known current or voltage may be applied between the electrodes 52, 53 and the resulting potential or current flow between the electrodes 52, 53 may be measured by a voltmeter or electrometer 55. The resistivity change caused by the adsorption of the sulfur compounds onto the microstructures 31 (FIG. 1) of the zinc oxide coating 54 may be manipulated by doping, changing the distance between the electrodes 52, 53, the pattern of the electrodes, etc. so the overall resistance falls within a suitable range for measurement.

The disclosed sulfur sensor and measurement system is designed based on the physical adsorption of organo-sulfur compounds onto zinc oxide. The inventors have surprisingly found that the rate of physical adsorption of organo-sulfur compounds onto zinc oxide may be a function of the crystallinity of the zinc oxide and the orientation of the crystallinity of the zinc oxide in the (002) plane, or a plane that protrudes outward from the substrate 30 or electrode in FIG. 1 or outward from the surface 33 of the first electrode 32 as shown in FIG. 2. As explained below, it has also been surprisingly found that the rate of physical adsorption is also dependent upon the rod-like or ribbon-like morphology of the zinc oxide coating and the oxygen deficiency of the zinc oxide coating.

The physical adsorption of organo-sulfur compounds onto zinc oxide is based, at least in part, on the good sorption affinity of zinc oxide with organo-sulfur compounds because of the crystal phase in the zinc oxide coating or microstructures. The physical adsorption of organo-sulfur compounds onto zinc oxide protrusions results in a change in the resistivity of the outer layer of the zinc oxide microstructures. The amount of change in resistance of the zinc oxide microstructures corresponds directly to the amount of sulfur compounds in the liquid available to react with the zinc in the zinc oxide microstructures 31. In FIG. 2, this change in resistivity can be measured by measuring a voltage change between first and second electrodes 32, 35. Further, as shown below, sulfur concentrations can be determined by measuring the amount of time it takes for the voltage to stabilize.

Figure 7:
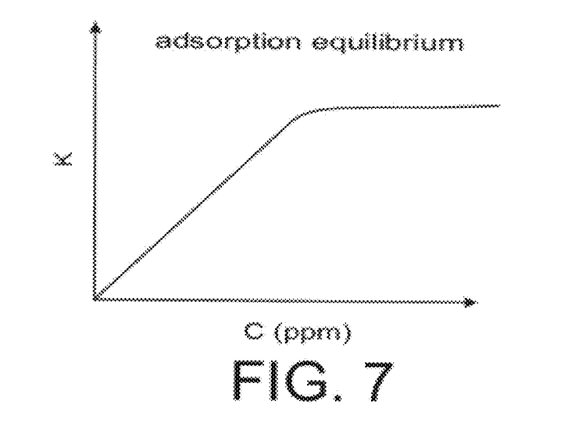
FIG. 7 graphically illustrates the ability of a disclosed zinc oxide sensor to adsorb sulfur until the sulfur concentration reaches a certain value, which is indicative of the concentration of sulfur and the liquid.

Referring to FIG. 2, in one aspect, a substrate 30 with a zinc oxide coating (not shown) on the surface 33 of the substrate 30 is at least partially submerged in a liquid 34. A second electrode 35 is also at least partially submerged in the liquid 34. The first and second electrodes 32, 35 are coupled to a potentiometer, electrometer or voltmeter 36. As the adsorption of sulfur compounds onto the zinc oxide microstructures 31 (FIG. 1) on the surface 33 proceeds, equilibrium will be established based on the concentration of sulfur compounds in the liquid being measured, as illustrated in FIG. 7.

Figure 3:
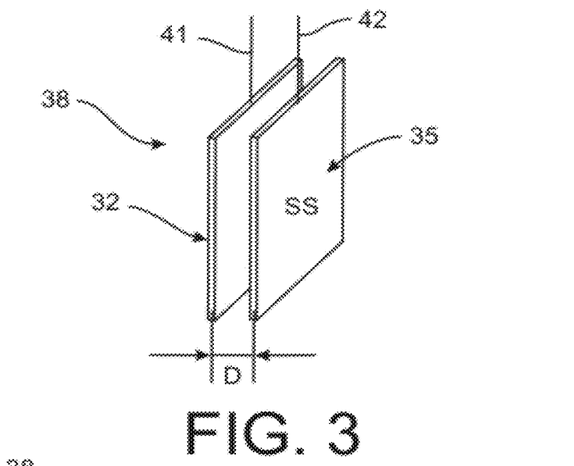
FIG. 3 is a perspective and schematic view of a disclosed sensor including a first electrode spaced apart from a second electrode by a predetermined distance in whereby both electrodes are connected to a potentiometer, an electrometer or voltmeter.

FIG. 3 illustrates an improved configuration for a sensor 38 that provides faster and more liable results than the sensor 37 of FIG. 2. The sensor 38 includes a first electrode 32 that is spaced apart from the second electrode 35 by a distance D that can range from about 0.2 to about 4 mm with one particular embodiment being about 0.4 mm. The first and second electrodes 32, 35 are connected to wires 41, 42 that are coupled to a potentiometer, electrometer or voltmeter 36 as illustrated in FIG. 2.

The size of the first and second electrodes 32, 35 may vary greatly as can the spacing between first and second electrodes 32, 35. For example, the widths of the first and second electrodes 32, 35 may be at least about 10 mm and the lengths of the first and second electrodes 32, 35 may be at least about 25 mm. Successful dimensions include 17 mm by 34 mm and 33.8 mm by 84.6 mm. For both sets of dimensions, the gap distance D was set at about 0.4 mm.

Because the disclosed sulfur measurement systems may be used in dielectric fluids, such as fuels, including diesel fuels, it has been found that the resistance between the second electrode 35 and the first electrode 32 may be too high to allow accurate voltage measurement in an open circuit potential arrangement, such as that shown in FIG. 2. It has also been found that positioning factors like distance and orientation of the second electrode 35 may introduce capacitive noise. As a result, the inventors surprisingly found that increasing the surface area of the second electrode 35 from a rod-like structure to a plate-like structure and decreasing the distance D between the first and second electrodes 32, 35 may simultaneously reduce resistance and increase capacitance. For example, using a gap distance D of 3 mm and changing the second electrode 35 from a rod-like structure to a plate-like structure of the same or similar dimensions as the first electrode 32 reduces the resistance between the first and second electrodes 32, 35 by a factor of about 60 thereby increasing the capacitance of the sensor 38 shown in FIG. 3 to about 60 times the capacitance of the sensor 37 shown in FIG. 2. Two dimensions that have been found to be suitable for stainless steel first and second electrodes 32, 35 include 17 mm by 34 mm and 33.8 mm by 84.6 mm. Of course, other sizes and dimensions are possible as will be apparent to those skilled in the art.

Figure 4:
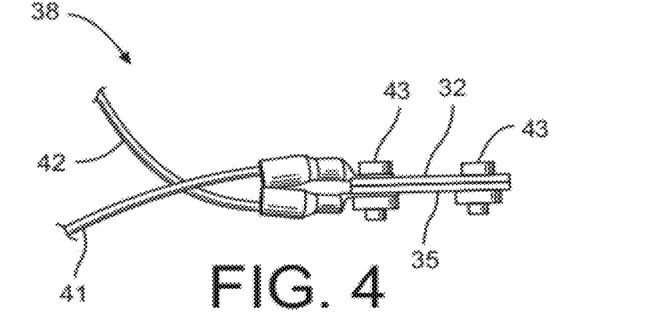
FIG. 4 is a side plan view illustrating the coupling of a second electrode to a first electrode by fasteners fabricated from insulating material.
Figure 5:
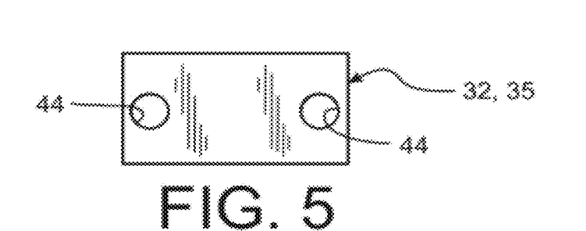
FIG. 5 is a plan view of one disclosed shape for a first and/or second electrode.
Figure 6:
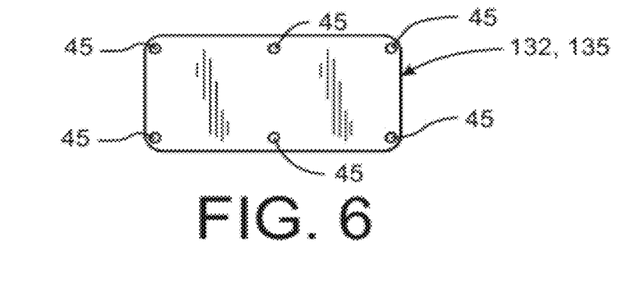
FIG. 6 is a plan view of yet another disclosed shape for a first and/or second electrode.

FIG. 4 illustrates the sensor 38 shown in FIG. 3 with a plurality of fasteners 43 to couple the electrodes 32, 35 together with a fixed spaced-apart distance D. The fasteners 43 should be fabricated from an insulating material, including, but not limited to polytetrafluoroethylene, a polyamide or a polyimide. The electrodes 32, 35 are coupled to a potentiometer, voltmeter or electrometer 36 (FIG. 2) by the conductive wires 41, 42. In FIG. 5, the electrodes 32, 35 are provided with two openings 44 for accommodating the insulating fasteners 43. FIG. 6 shows an alternative working or second electrode 132, 135 with six openings 45 for accommodating insulating fasteners.

In FIG. 7, the X axis is the concentration of sulfur compounds in the liquid being measured and the Y axis is the equilibrium constant for the adsorption of the sulfur compounds onto the zinc oxide microstructures. As can be seen in FIG. 7, once a certain concentration is reached, the adsorption equilibrium constant becomes the same for higher concentrations. Thus, as explained below, depending upon the crystallinity in the (002) plane, the morphology of the zinc oxide microstructures and the oxygen deficiency of the zinc oxide coating, various sensor coatings can be provided that will be effective at measuring various sulfur concentrations.

Figure 8:
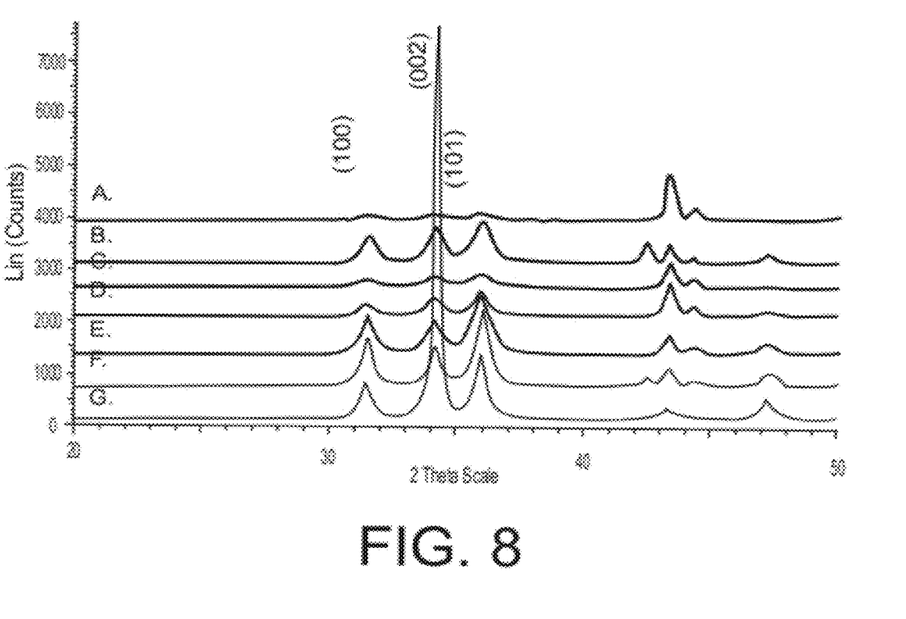
FIG. 8 graphically illustrates x-ray diffraction spectrums for seven different zinc oxide coatings (A-G) that were generated using either different precursors and/or different reaction conditions.

As indicated above, a high crystallinity in the (002) plane (generally perpendicular to the substrate or electrode) may be an indication of good adsorption of sulfur compounds onto the zinc microstructures. Turning to FIG. 8, x-ray diffraction spectrums are graphically illustrated for seven different samples A-G. Crystallinity in the (002) plane is indicated by a peak at or about 34 along the X axis (2-theta scale). Thus, samples A and C show no or minimal crystallinity along the (002) plane while samples B and D-G show crystallinity along the (002) plane with sample G showing the highest level of crystallinity along the (002) plane.

Figure 9:
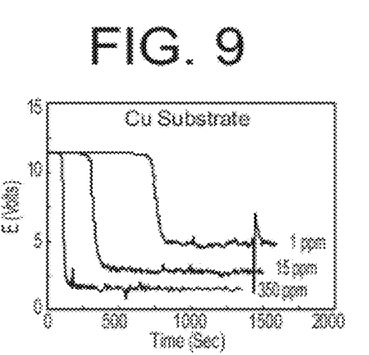
FIG. 9 graphically illustrates the ability of the zinc oxide coating disposed on a copper substrate as shown in the photograph of FIG. 10 to adsorb sulfur in a liquid at concentrations ranging from 1 ppm to 350 ppm.
Figure 10:
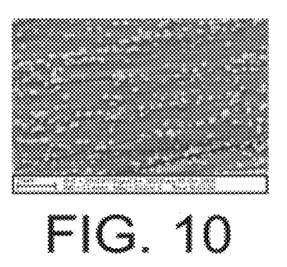
Figure 11:
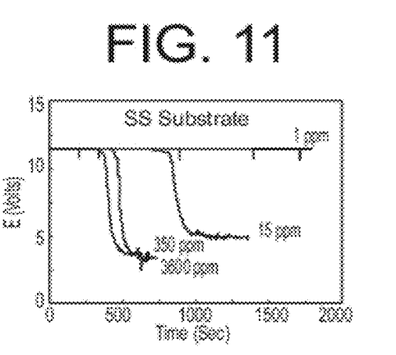
FIG. 11 graphically illustrates the ability of a disclosed zinc oxide coating on a stainless steel substrate as shown in FIG. 12 to adsorb sulfur in a liquid at concentrations ranging from 15 ppm to 3600 ppm.
Figure 12:
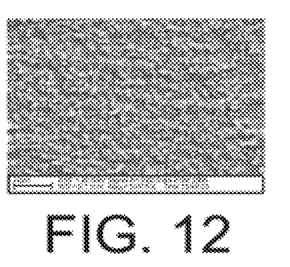

Turning to FIGS. 9-12, comparisons of different electrodes and different coating densities are provided. In FIG. 9, a copper electrode was coated with zinc oxide as shown in FIG. 10, but when compared with FIG. 12, the zinc oxide coating of FIG. 10 is less dense than the zinc oxide coating of FIG. 12, which was coated onto a stainless steel electrode. The less dense coating of FIG. 10, as shown in FIG. 9, detects sulfur at low concentrations of 1 ppm and 15 ppm as well as at higher concentrations of 350 ppm. The higher concentration of 350 ppm was detected by the coating of FIGS. 9-10 faster than the concentrations at 15 ppm and 1 ppm. In contrast, the dense coating of FIG. 12 cannot detect sulfur compounds at low concentrations of about 1 ppm, but can detect sulfur compounds at higher concentrations of 15 ppm, 350 ppm and 3600 ppm. The electrode of FIGS. 9-10 also detected concentration of 15 and 350 ppm at a much faster rate than the electrode of FIGS. 11-12. Thus, from FIGS. 9-12, it can be concluded that denser coatings of zinc oxide are more useful for higher concentrations of sulfur compounds in a liquid and less dense coatings of zinc oxide are more useful for faster measurements of lower concentrations of sulfur compounds in a liquid.

Figure 13:
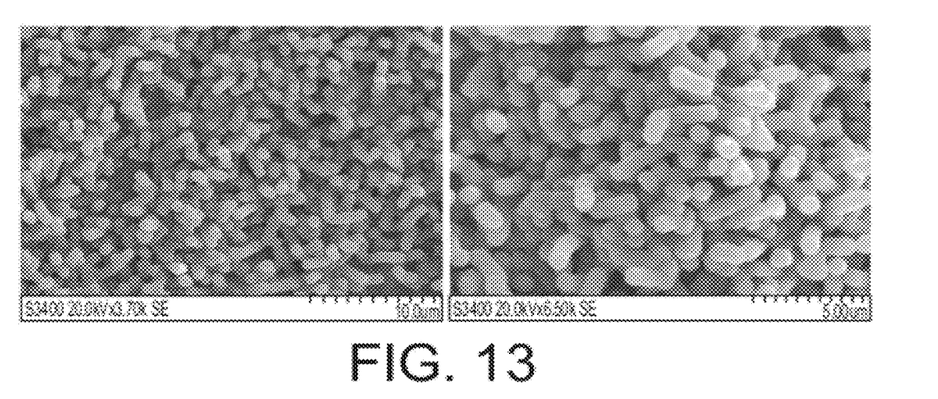
FIG. 13 shows two SEM photographs of different magnifications of a zinc oxide coating that includes rod-like or ribbon-like microstructures that protrude upwardly from the substrate and that can adsorb sulfur compounds as illustrated in FIG. 14.

Turning to FIG. 13, two SEM photographs, of different magnifications, are shown of the same coating. The sample of FIG. 13 was prepared using a furnace temperature of 500° C. and an increased manifold temperature of 300° C. A zinc acetylacetone precursor was utilized and the coating process was carried out for two hours at a pressure of 10 torr. The argon and oxygen flow rates were 50 ml/min. This procedure produced an oxygen deficient zinc oxide coating as shown in FIG. 13, with excellent rod-like structures that protrude upwardly from the substrate (not shown) and therefore have a high crystallinity in the (002) plane. The oxygen deficiency was established by measurement which revealed that the coating of FIG. 13 included 3.31 wt % carbon, 17.9 wt % oxygen, 1.04% chromium, 4.53% iron and 73.22% zinc. The ratio of zinc to oxygen for a fully saturated zinc oxide (ZnO) coating is 3.75, or the molecular weight of zinc (30) divided by the molecular weight of oxygen (8). Hence, the 4.09 ratio (73.22/17.9) is indicative of an oxygen deficient zinc oxide coating.

Figure 14:
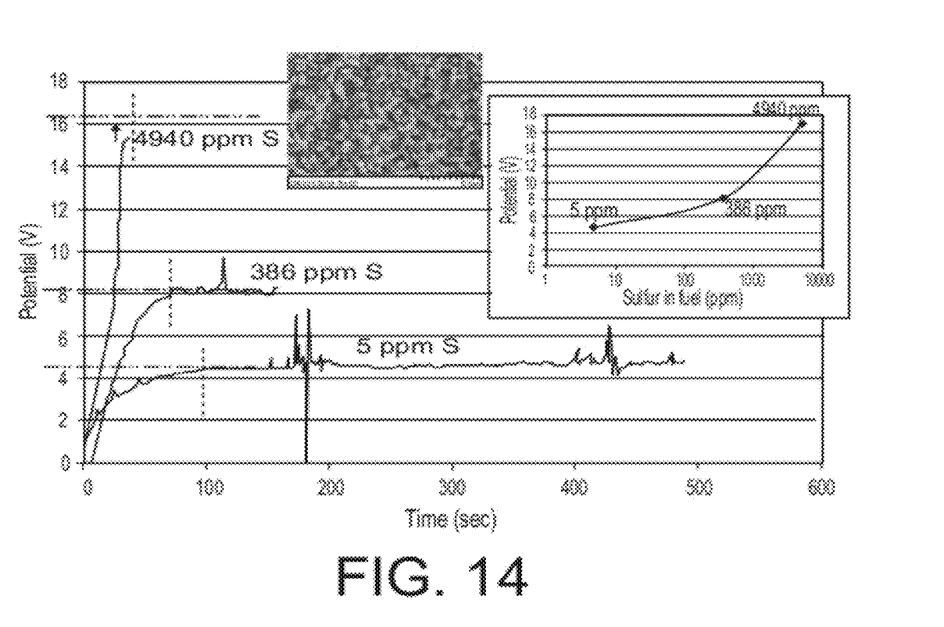
FIG. 14 graphically illustrates an ability of the coating shown in FIG. 13 to adsorb and detect sulfur at a concentration of 5 ppm in about 100 seconds and the ability to adsorb and detect sulfur at a concentration of about 386 ppm in about 80 seconds and FIG. 14 also graphically illustrates the sensitivity of the sensor made from the coating of FIG. 13.

FIG. 14 illustrates, graphically, the response of a sensor coated with the coating of FIG. 13 to liquids having differing amounts of sulfur compounds, specifically 5 ppm and 386 ppm. The voltmeter utilized for the measurements illustrated in FIG. 14 was not capable of detecting more than 15 volts and therefore the combination of the sensor and voltmeter used for FIG. 14 cannot adequately detect a concentration of 4940 ppm as shown in FIG. 14. FIG. 14 also illustrates that the 0.7 micron thick rod-like structures of the coating of FIG. 13 provide a sensor that is suitable for both low sulfur compound detection (5 ppm) and relatively high sulfur detection (386 ppm). Further, the response time is substantially reduced to about 100 seconds for the 5 ppm sulfur compound concentration liquid and about 80 seconds for the 386 ppm sulfur compound concentration liquid.

Figure 18:
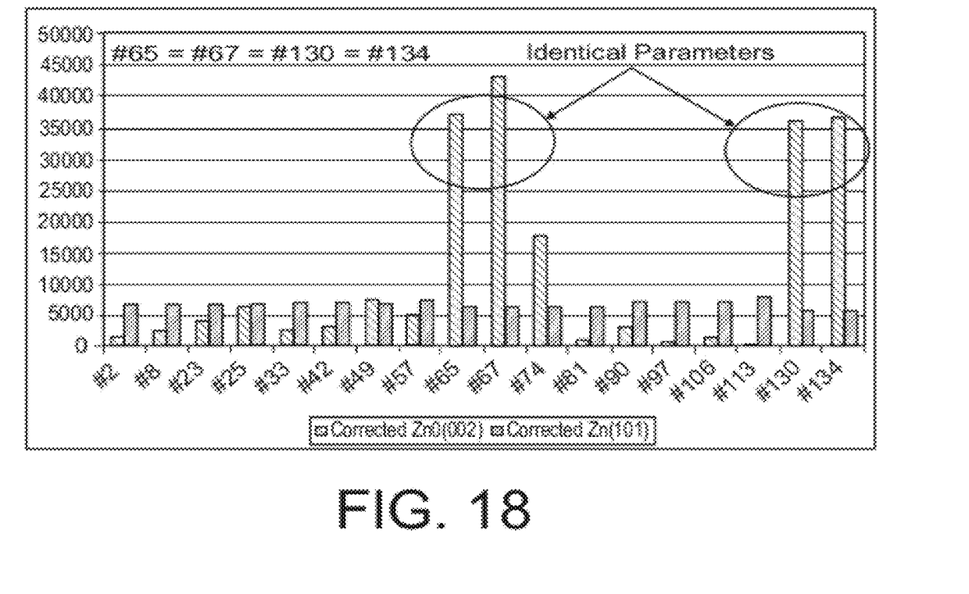
FIG. 18 graphically illustrates the crystallinity of 18 zinc oxide coatings, especially the high crystallinity of four of the zinc oxide coatings in the (002) plane, specifically sample numbers 65, 67, 130 and 134, which were fabricated using the same process parameters.
Figure 19:
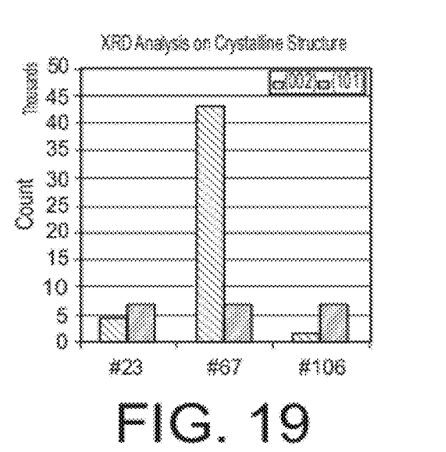
FIG. 19 also graphically illustrates the high crystalline structure in the (002) plane of sample number 67 in comparison to sample numbers 23 and 106.

FIGS. 18-19 are bar graphs of the x-ray diffraction (XRD) analysis of the crystalline structures of zinc oxide coatings made with varying parameters. Specifically, the cycle time, vacuum pressure, bubbler temperature, manifold temperature set point and chamber temperature were all varied. Referring to FIG. 18, identical parameters were used for sample numbers 65, 67, 130 and 134. The parameters used to fabricate the sensor coatings of samples 65, 67, 130 and 134 are presented in the first or left column of Table 1 below. The parameters for the other samples illustrated in FIGS. 18 and 19 are also shown in Table 1.

Figure 15:
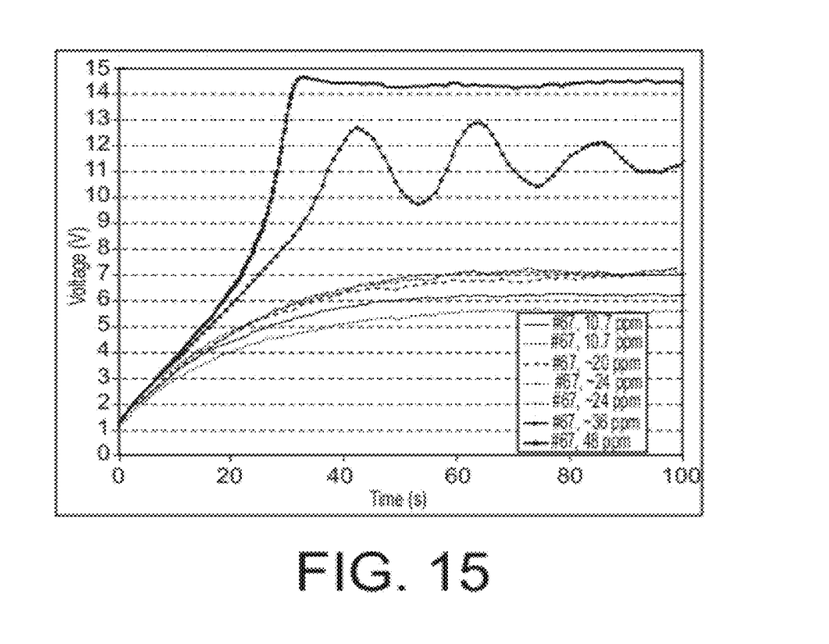
FIG. 15 graphically illustrates an ability of sample 67 of FIGS. 18-19 to detect sulfur and liquids at low concentrations (10.7 ppm to 48 ppm) and the increased sensitivity of sample 67 due to the high crystallinity in the (002) plane as shown in FIGS. 18-19.

FIGS. 15-20 illustrate the importance of high crystallinity in the (002) plane for the zinc microstructures 31 that are coated on to the first electrode 32. Specifically, in FIG. 15, sample number 67, which is graphically illustrated in FIGS. 18-19, exhibits a high crystallinity in the (002) plane as indicated in FIGS. 18-19. Sample 67 of FIG. 15 illustrates an ability to measure relatively low sulfur compound concentrations of 10.7 ppm, and concentrations in the 20-24 ppm range although the sensitivity between 20 ppm and 24 ppm is somewhat less than desirable. Sample 67 of FIG. 15 also exhibits an ability to detect or measure relatively high sulfur compound concentrations of 48 ppm as well as 36 ppm. The line for 36 ppm exhibits a fair amount of noise, which is attributable to environmental factors that can be controlled.

Figure 16:
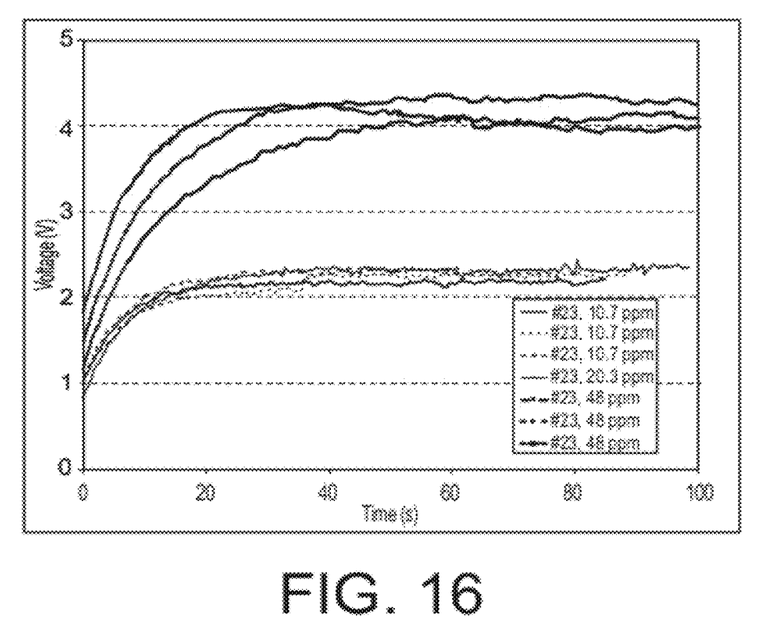
FIG. 16 graphically illustrates an ability of sample 23 of FIGS. 18-19 to detect sulfur and liquids at low concentrations (10.7 ppm, 20.3 ppm and 48 ppm) and the decreased sensitivity of sample 23 compared to sample 67 due to the relatively low crystallinity in the (002) plane as shown in FIGS. 18-19.
Figure 17:
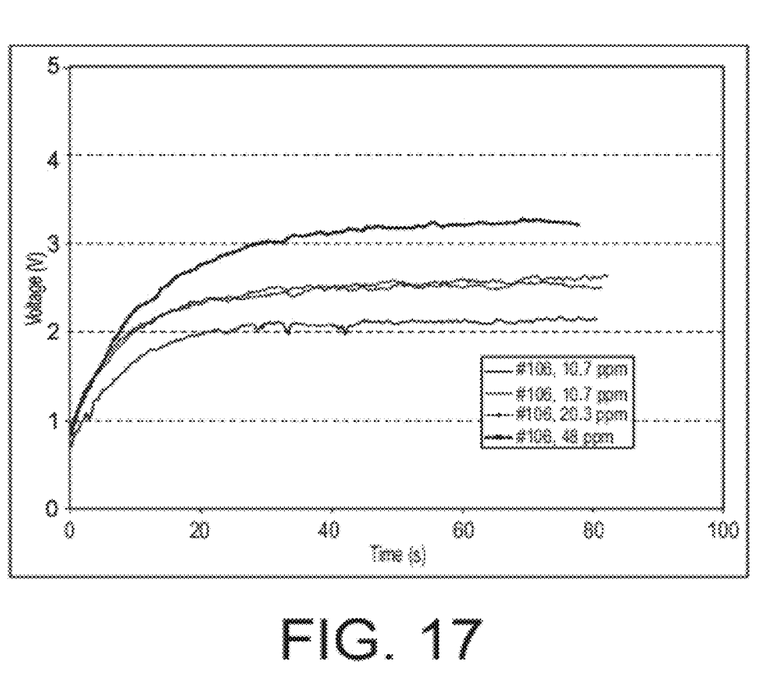
FIG. 17 graphically illustrates an ability of sample 106 of FIGS. 18-19 to detect sulfur and liquids at low concentrations (10.7 ppm, 20.3 ppm and 48 ppm) and the decreased sensitivity of sample 106 compared to sample 67 due to the relatively low crystallinity in the (002) plane as shown in FIGS. 18-19.

Turning to FIG. 16, sample 23 of FIGS. 18-19 is illustrated. FIGS. 18-19 show that sample 23 has a low crystallinity in the (002) range, which results in a first electrode coated with zinc microstructures, but which has relatively low sensitivity between 10.7 ppm and 20.3 ppm. The same can be said for sample 106 of FIG. 17 which, as shown in FIGS. 18-19, also exhibits low crystallinity in the (002) plane, thereby resulting in poor sensitivity between the 10.7 ppm and 20.3 ppm sulfur compound concentration.

From Table 1, it can be seen that multiple factors have an impact on the (002) crystal lattice orientation. Those factors include cycle time, vacuum pressure, bubbler temperature, manifold temperature and chamber temperature. It appears that the vacuum pressure and cycle time are primary factors and the manifold temperature, bubbler temperature and chamber temperature are secondary factors. With the high ratio of (002) orientation to (101) orientation provided by sample number 67, which was made using the same parameters at samples 65, 130 and 134, it is apparent that maintaining the vacuum pressure somewhat higher, at 15 torr and the cycle time at about 7 hours while maintaining the manifold temperature at about 225° C., the bubbler temperature at about 125° C. and, less importantly, the chamber temperature at about 500° C. will provide zinc oxide microstructures having a strong (002) orientation. Of course, these parameters can be varied greatly and parameters can be chosen for specific applications, such as ultra low sulfur fuels versus high sulfur fuels.

Figure 20:
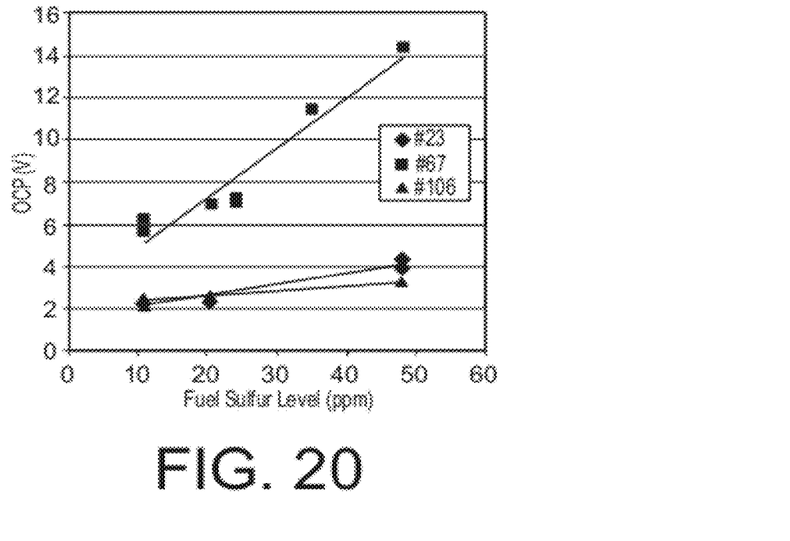
FIG. 20 graphically illustrates the increased sensitivity of sample 67 in comparison to samples 23 and 106.

Referring to FIG. 20, it is apparent that sample 67 provides the best sensitivity between the concentrations of 10.7 ppm and 48 ppm. It will also be noted that all samples became saturated or established equilibrium in relatively short time periods. Specifically, while somewhat slower than samples 23 (FIG. 16) and 106 (FIG. 17), sample 67 established equilibrium at the higher concentration of 48 ppm in about 30 seconds and established equilibrium at the lower concentrations in about 50 seconds.

Figure 21:
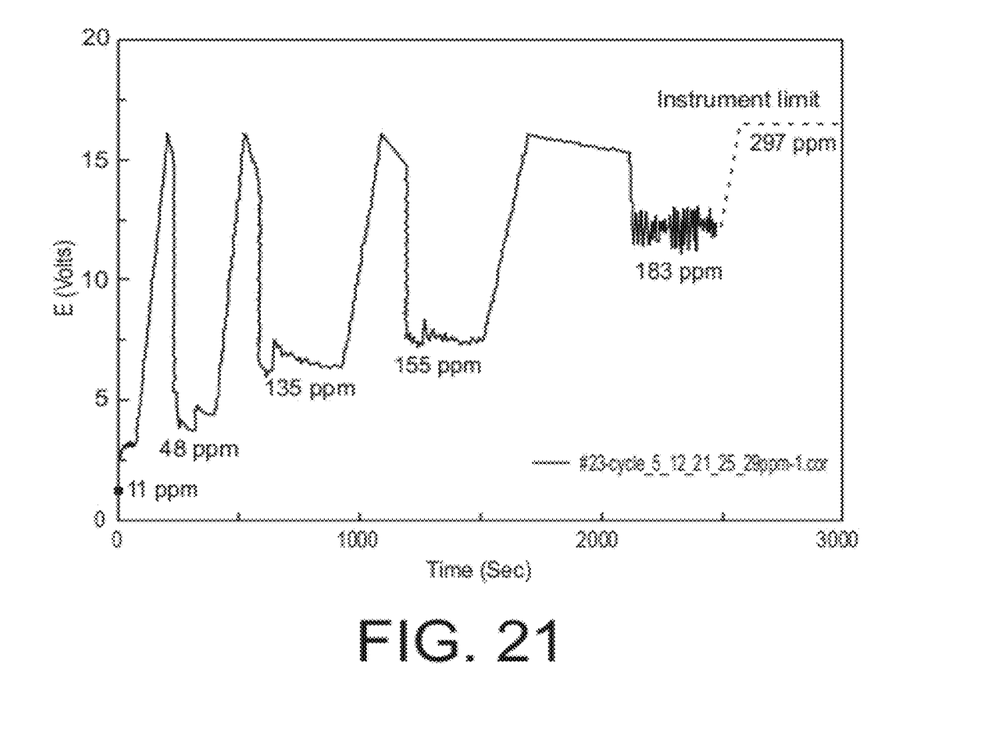
FIG. 21 graphically illustrates an improvement in the response of sample number 23 to various sulfur concentrations whereby the improvement in response is obtained by rinsing the sensor with pentane between measurements, the pentane rinses being indicated by the spikes in the curves between the stabilized voltage levels that are indicative of the sulfur concentrations.
Figure 22:
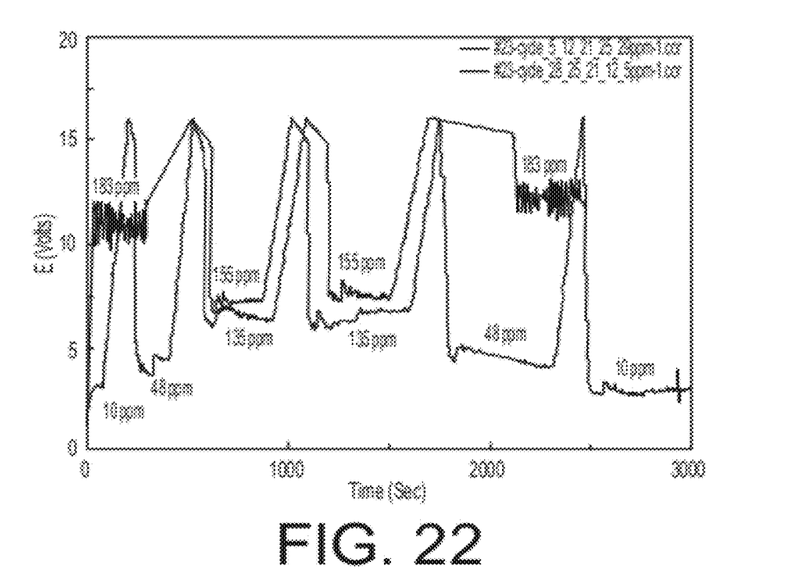
FIG. 22 is another graphic illustration of the repeatability of the measurements made by sample 23 wherein sample 23 was rinsed between measurements and the measurements are carried out twice and in different orders, thereby indicating the repeatability of the measurements made by sample 23.

Finally, FIGS. 21-22 illustrate the re-usability and repeatability of measurements using the disclosed sensors and measurement systems. Turning to FIG. 21, the voltage stabilizes at around 6 volts which correlates to a sulfur compound concentration in the liquid of about 11 ppm. The voltage also stabilizes at less than 5 volts, which correlates to a sulfur compound concentration of about 48 ppm. The voltage also stabilizes at about 7 volts, 7.5 volts and about 11 volts which correlate to sulfur compound concentrations of about 135, 155 and 183 ppm respectively. The instrument limit is about 15 volts, so concentrations higher than 297 ppm are not detectable by sample 23. The peaks between the stabilized voltage values indicate that the sensor was rinsed with pentane between exposures to the different liquids having different sulfur compound concentrations.

The repeatability of the measurements of sample 23 are illustrated in FIG. 22. Specifically, the exposure to the five different liquids, 11 ppm, 48 ppm, 135 ppm, 155 ppm and 183 ppm were reversed and pentane rinses were carried out after the sensor was exposed to one liquid and before the sensor was exposed to the next liquid. The stabilized voltage values for 11 ppm, 48 ppm, 135 ppm, 155 ppm and 183 ppm sulfur compound concentrations are about equal for both cycles.

TABLE 1

| Sample # | 67 | 25 | 49 | 57 | 74 | 90 |
| --- | --- | --- | --- | --- | --- | --- |
| Cycle time (hrs) | 7 | 8 | 8 | 5 | 4 | 4 |
| Vacuum pressure (torr) | 15 | 2.5 | 2.5 | 10 | 2.5 | 2.5 |
| Ar flow rate (sccm) | 50 | 50 | 50 | 50 | 50 | 50 |
| $O_2$ flow rate (sccm) | 50 | 50 | 50 | 50 | 50 | 50 |
| Bubbler temp. (° C.) | 125 | 125 | 125 | 125 | 110 | 125 |
| $O_2$ inlet temp. (° C.) | 200 | 250 | 250 | 200 | 200 | 200 |
| Manifold temp. (° C.) | 225 | 265 | 250 | 225 | 225 | 225 |
| Chamber flange temp (° C.) | 522-527 | 477-487 | 495-499 | 525-532 | 527-529 | 527-529 |
| Corrected (002) | 43119 | 6446 | 7640 | 4777 | 17734 | 3380 |
| Corrected (101) | 6634 | 6939 | 7082 | 7671 | 6536 | 7411 |
| (002)/(001) | 6.5 | 0.93 | 1.08 | 0.62 | 2.71 | 0.46 |

INDUSTRIAL APPLICABILITY

The measurement system disclosed herein is particularly useful in field applications to allow operators to determine the sulfur content of a fuel before introducing the fuel into a machine that may be designed to run on fuels having specific sulfur concentrations. The measurement system disclosed herein may be modified so the sensor or pair of electrodes is disposable, reusable, or the system may be used as an on-board measurement system that determines the sulfur content of the fuel in the fuel tank neck before an appreciable amount of fuel is introduced.

As shown in FIG. 14, one disclosed sensor shows good sensitivity at both low (5 ppm) and higher (386 ppm) concentrations. The sensor of FIG. 14 reached a saturation point in about 100 seconds for the 5 ppm liquid while the sensor of FIG. 15 reached a saturation point for all concentrations in less than or about one minute. Thus, the disclosed sensors and measurement systems are fast enough to be used in the field with minimal inconvenience.

As an alternative, an operator may monitor the amount of time necessary for saturation of a ZnO sulfur sensor, as indicated by stabilization of the voltage across the sensor while the current remains constant. The operator could correlate the stabilized voltage to a sulfur content using a lookup table, or the correlation could be automated using known automating techniques, such as a computer accessing a series of lookup tables, and an absolute sulfur reading could be issued to the operator.

To form the ZnO microstructures on a substrate, any suitable deposition and/or growth method known in the art may be used. For example, as noted above, MOCVD may be used to form ZnO deposits on a conductive or ceramic substrate. FIG. 18 and Table 1 show the affect of the vacuum pressure and cycle time or time of the deposition on the (002) crystallinity, while secondary factors are the manifold temperature and bubbler temperature. FIG. 13 shows suitable ZnO microstructures that may be grown over about two hours, whereas denser and thicker ZnO microstructures may be grown under the same conditions over about 3.5 hours. The thickness of the ZnO micro-structures shown in FIG. 13 is about 0.7 microns and the density is appropriate to allow the ZnO microstructures to grow in highly random directions away from the substrate. By comparison, increasing the deposition time to 3.5 hours results in a thickness of the ZnO microstructures of about 1.0 microns. While this thickness in itself is acceptable, the density of the ZnO on the surface of the conductive substrate may be too high for low concentrations of sulfur compounds as a high density inhibits interaction between the microstructures and the liquid. Such a high density may force the ZnO microstructures to grow in a highly compact, ordered fashion away from the substrate. Thus, two or more sensors may be employed for fuels of different sulfur concentrations.

While this disclosure has referred to the microstructures as being ZnO microstructures, one skilled in the art should appreciate that the microstructures may have incidental amounts of other elements, likely drawn from the substrate during the deposition and growth process. For example, when the conductive substrate is a stainless steel, the microstructures may have between about 1.0-5.0 wt % C, between about 14.0-24.0 wt % O, between about 0.5-1.5 wt % Cr, and between about 2.5-7.0 wt % Fe, the balance being Zn. In one example, analysis showed that ZnO microstructures grown on a stainless steel substrate had the following composition, by weight percent: C—3.31; O—17.90; Cr—1.04; Fe—4.53; and Zn—73.22.

Regarding the time necessary to accurately measure the sulfur compound content in the liquid, among other factors, as shown in FIGS. 9, 11, 14-17, 21 and 22, this is highly dependent on the electrode material and dimensions, the spacing between the electrodes, the total surface area of the ZnO microstructures exposed to the liquid, and the sulfur concentration of the liquid. As can be seen from the data, as sulfur level of the liquid increases, the response time decreases and the stabilized voltage increases when a ZnO sulfur sensor formed in accordance with this disclosure is used to measure the sulfur level of fuel.

FIGS. 23-24 disclose a compact, easy to manufacture system whereby the electrodes 52, 53 may be formed on an insulating substrate, such as a silicon substrate, before a zinc oxide coating 54 is applied thereon, using the techniques described above.

What is claimed is:

1. A sulfur concentration measurement system for liquids, comprising:
    an insulating substrate;
    a first electrode formed on the insulating substrate;
    a second electrode formed on the insulating substrate and spaced apart from the first electrode;
    zinc microstructures that are oxygen deficient and have a crystal lattice structure at least partially oriented in the (002) plane and at least partially cover the insulating substrate, the first electrode, and the second electrode, and
    an electrometer for measuring a voltage between the first and second electrodes.

2. The system of claim 1 wherein the zinc oxide microstructures have a crystal lattice structure that is at least partially oriented in the (002) plane.

3. The system of claim 1 wherein the first and second electrodes are plates disposed at least substantially parallel to each other and spaced apart by a predetermined distance.

4. The system of claim 3 wherein the predetermined distance ranges from about 0.2 to about 4 mm.

5. The system of claim 3 wherein the predetermined distance is about 0.4 mm.

6. The system of claim 1 wherein the first and second electrodes include stainless steel plates disposed at least substantially parallel to one another.

7. The system of claim 1 wherein the first and second electrodes are coupled together but spaced apart at least substantially parallel to one another by at least one fastener fabricated from at least one insulating material.

8. The system of claim 7 wherein the insulator fastener is selected from the group consisting of polytetrafluoroethylene, a polyamide and a polyimide.

9. The system of claim 1 wherein the zinc oxide microstructures are rod-like or ribbon-like in form.

10. The system of claim 9 wherein the zinc oxide microstructures are at least about 0.1 microns wide.

11. The system of claim 9 wherein the zinc oxide microstructures are between about 0.1 microns and about 3 microns wide.

12. The sensor of claim 9 wherein the zinc oxide microstructures protrude from the substrate at least about 0.1 micron.

13. The system of claim 9 wherein the zinc oxide microstructures protrude from the substrate between about 0.1 micron and about 0.3 mm.

14. The sensor of claim 1 wherein the first and second electrodes have widths of at least about 10 mm, lengths of at least about 25 mm and the first electrode is spaced apart from the second electrode by a gap ranging from about 0.2 to about 0.6 mm.

15. The system of claim 14 wherein the widths and lengths of the first and second electrodes are about equal.

16. The system of claim 1 wherein the first electrode is formed on an insulating substrate.

17. A sulfur concentration measurement system, the measurement system comprising:
   a sensor including a substrate, the substrate being partially covered by a first electrode and by a second electrode, the first and second electrodes being spaced-apart from each other on the substrate, the substrate and electrodes being coated with zinc oxide microstructures, the zinc oxide microstructures having crystal lattice structures oriented in the (002) plane and that are oxygen deficient;
   a current source applied between two spaced-apart points on the zinc oxide microstructures; and
   a voltage detector coupled to the first and second electrodes.

18. The sulfur concentration measurement system of claim 17 wherein the zinc oxide microstructures are rod-like or ribbon-like in form.

19. The sulfur concentration measurement system of claim 17 wherein the voltage detector is an electrometer.

20. A sulfur concentration measurement system, the measurement system comprising:
   a sensor including a substrate, the substrate being partially covered by a first electrode and by a second electrode, the first and second electrodes being spaced-apart from each other on the substrate, the substrate and electrodes being coated with zinc oxide microstructures, the zinc oxide microstructures having crystal lattice structures oriented in the (002) plane and that are oxygen deficient;
   a voltage source applied between two spaced-apart points on the zinc oxide microstructures; and
   a current detector coupled to the first and second electrode.

21. The sulfur concentration measurement system of claim 20 wherein the zinc oxide microstructures are rod-like or ribbon-like in form.

22. The sulfur concentration measurement system of claim 20 wherein the current detector is an electrometer.

23. A method for determining a sulfur concentration in a liquid, the method comprising:
   exposing the liquid to a sulfur sensor, the sulfur sensor including a first electrode at least partially covered with zinc oxide microstructures protruding from the first electrode, at least some of the zinc oxide microstructures having a crystal lattice structure oriented in the (002) plane, the sulfur sensor also having a second electrode coupled to but spaced apart from the first electrode and disposed at least substantially parallel to the first electrode;
   monitoring a voltage between the first and second electrodes; and
   after the voltage has stabilized, correlating the voltage to a sulfur concentration in the liquid.

24. A method for determining a sulfur concentration in a liquid, the method comprising:
   exposing the liquid to a sulfur sensor, the sulfur sensor including a substrate partially covered by a first electrode and partially covered by a second electrode, the first and second electrodes being spaced apart from each other on the substrate, the first and second electrodes and the substrate being at least partially covered with zinc oxide microstructures protruding from the first electrode, at least some of the zinc oxide microstructures having a crystal lattice structure oriented in the (002) plane;
   applying one of a constant current or constant voltage between two spaced apart points on the zinc oxide;
   monitoring one of a voltage or a current between the first and second electrodes; and
   after the voltage or current has stabilized, correlating the voltage to a sulfur concentration in the liquid.

* * * * *